United States Patent [19]
Paton et al.

[11] Patent Number: 6,113,908
[45] Date of Patent: Sep. 5, 2000

[54] METHODS FOR PROCESSING OAT GROATS AND PRODUCTS THEREOF

[75] Inventors: David Paton; Martin J. T. Reaney; Nancy J. Tyler, all of Saskatoon, Canada

[73] Assignee: Her Majesty the Queen in right of Canada, as represented by the Minister of Agriculture, Ottawa, Canada

[21] Appl. No.: 09/273,715

[22] Filed: Mar. 22, 1999

[51] Int. Cl.[7] .............................. A61K 35/78; A23D 9/00; C12S 3/02; C07H 1/08
[52] U.S. Cl. ................ 424/195.1; 426/417; 426/430; 426/429; 426/483; 435/274; 435/277; 536/123.12; 536/128
[58] Field of Search .................. 424/195.1; 426/417, 426/430, 429, 483; 435/274, 277, 198; 536/123.12, 128

[56] References Cited

U.S. PATENT DOCUMENTS

| | | | |
|---|---|---|---|
| 3,640,728 | 2/1972 | Ronai et al. | 426/380 |
| 4,053,492 | 10/1977 | Boocock et al. | 426/417 |
| 5,169,660 | 12/1992 | Collins et al. | 426/271 |

OTHER PUBLICATIONS

Doehlert et al, Cereal Chem. 74(4): 403–406, 1997.

*Primary Examiner*—Francisco Prats
*Attorney, Agent, or Firm*—Richard J. Hicks

[57] ABSTRACT

Methods of treating dehulled or hull-less oat, i.e. oat groats, to produce oat pearlings, oat flour and oat bran products are described. Oat groats are abrasion milled to remove up to 15% by weight and produce pearled oat groats and pearlings. The pearlings are extracted sequentially with aqueous ethanol and hexane to produce an anti-irritant and a light oat oil, or with hexane to produce a dark oat oil and lipase. The pearled oat groats are steeped in an aqueous medium for up to 4 hours and then macerated to produce an enriched oat bran, from which an enriched beta glucan may be extracted; a refined oat flour, from which oat starch and oat protein may be extracted; and a pearled oat groat extract from which further products, such as an oat anti-irritant can be recovered.

14 Claims, 1 Drawing Sheet

METHODS FOR PROCESSING OAT GROATS AND PRODUCTS THEREOF

FIELD OF INVENTION

This invention relates to novel methods for processing oat (Avena sp. L.) groats. More particularly the invention relates to pearling oat groats and recovering a plurality of products from the various fractions thereof.

BACKGROUND OF INVENTION.

As used in this specification the term 'oat groats' means dehulled oat grains or hull-less oat grains, where oat is defined as referring to all members of the genus Avena.

Traditionally, oat is not the subject of detailed fractionation into discreet components or fractions of specific composition of matter. Current commercial practice is limited to dry milling and screening of either enzyme-inactivated oat groats or oat flake (rolled oats) to give a coarse fraction known as 'oat bran' and a finer fraction known as 'oat flour'. Several process prototypes describe ways of obtaining purer brans and flours. Hohner and Hyldon in U.S. Pat. No. 4,028,468, 1977, describe a process which first involves hammer milling of the oat groat prior to any wet fractionation taking place. A drawback of this approach lies in the fact that any random dry comminution produces a spectrum of particle sizes which places constraints on downstream separation or screening equipment. Myllymaki et al., in U.S. Pat. No. 5,312,636, 1994, employed a roller mill followed by screening to obtain a crude oat bran which then must be refluxed in 80% isopropyl alcohol to inactivate the lipase known to be present in this fraction. Lehtomaki et al. in U.S. Pat. No. 5,183,677 1993) described a process in which oats were rapidly ground in cold water <8° C., homogenized and screened to give a bran product stated to contain beta-glucan in the range 15–40% by weight. Few operating details were recited in this disclosure to allow anyone skilled in the art to practice the invention. No mention was made of the nature or composition of the remaining material not recovered in this process. Burrows et al., in Canadian Patent 1,179,189, 1984 described a process which took advantage of the selective activity of endosperm cell wall degrading enzymes to effectively fractionate the bran from the flour but the products were unstable due to rancidity. Collins and Paton, in U.S. Pat. No. 5,169,660, 1992 made improvements to the Burrows et al. technology by employing 80% aqueous alcohol as the wet milling medium following a steeping period, which produces stable products without the need for refluxing. Although separation efficiencies have been demonstrated in these processes, the total process time can be in excess of 30 h which is considered too lengthy for full commercial implementation.

Oat has long been known to contain a gummy substance commonly referred to as beta-glucan. This non-starch polysaccharide is composed of glucose units joined together in contiguous runs of beta 1,3 and beta 1,4 linkages. Although there has been an interest in this substance for both food and non-food uses for many years (Hohner & Hyldon, U.S. Pat. No. 4,028,468; Goering et al. U.S. Pat. No. 4,804,545; Lehtomaki et al. U.S. Pat. No. 5,106,640 and U.S. Pat. No. 5,183,677; Myllymaki et al. U.S. Pat. No. 5,312,636; Bhatty U.S. Pat. No. 5,518,710), a satisfactory process to isolate and prepare the polysaccharide in high purity and in a functionally useful form has not yet been developed. Most attempts to prepare oat beta-glucan have involved using either ground oat flake or a sifted fraction therefrom commonly referred to as oat bran. It has also been recognized that oats contain an enzyme, beta-glucanase, which unless inactivated, will rapidly de-polymerize the beta-glucan in aqueous solution/dispersion. Current methods of inactivation commonly employ a combination of heat, moisture and time.

Current attempts to prepare oat beta-glucan at the commercial level are less than successful from several standpoints. Firstly, oat groats nominally contain 3–5% beta-glucan which is not sufficiently high to be economically attractive. Also, in the course of enzyme inactivation, some of the oat starch may be structurally altered and the protein denatured which renders a total recovery of oat components in a functional form somewhat deficient. Current approaches also make use of repeated or sequential treatments involving alkaline extraction and acid neutralization. This can result in a high residual protein content in the final product, product discolouration and lower functional viscosity.

In U.S. Pat. No. 5,169,660, Collins and Paton describe the steeping of whole oat groats and their subsequent wet milling and screening in aqueous alcohol, which yields a bran depleted in flour but enriched in beta-glucan gum, and a flour that is depleted in bran but enriched in starch and protein. In order to loosen the sub-aleurone bran layers from the inner endosperm, the groats must be steeped in water for up to 24 h with total processing time around 30 h. The long processing time translates into increased equipment and labour costs and limits the volume of oats that may be processed per unit time. Further, our prior invention requires a working concentration of 80% w/w of an aliphatic alcohol which further makes the process costly to operate.

Exposure of skin to chemicals contained in topical cosmetic and pharmaceutical compositions can result in adverse reactions, including irritation response and contact sensitization of the skin. As used herein, the term cosmetic and pharmaceutical composition is used in the widest sense and encompasses any composition that is applied to the skin for a beneficial effect. As used herein, contact sensitization of the skin refers to adverse systemic immunological reactions of the skin, e.g. itching, burning, swelling or redness. Irritation response of the skin involves similar symptoms in which the systemic immune system plays no role.

A small but significant segment of the population is particularly prone to such irritation response and contact sensitization of the skin. As a consequence, the use of a wide variety of topical preparations for the skin by this segment of the population is at best, an unpleasant task. For example, compositions containing paraminobenzoic acid (sunscreens) or Balsam of Peru are known to cause contact sensitization, and certain chemicals, e.g. vasodilators and surfactants are known to cause irritation response when used by some people.

In addition, certain types of physical contact with human skin can cause irritation. For example, the removal of hair from human skin by waxing methods is known to cause some degree of irritation to most, if not all, persons. Hereinafter, the types of physical contact that cause irritation response of human skin are referred to as 'contact physical irritants'.

Anti-irritants can be derived from mineral and botanical sources. For example, extracts of seeds of *Cola nitida* (Vent.)A.Chev. can be added to cosmetics to achieve an anti-irritant effect (U.S. Pat. No. 5,028,428). Furthermore, salts of strontium are also capable of suppression of irritation response to contact physical irritants (U.S. Pat. No. 5,716,625). Oat groats are known to contain anti-irritants but no commercial method or patent has led to a means to concentrate such an anti-irritant. A preferred embodiment of the present application describes the extraction of a dry powdered anti-irritant or a dissolved form oat based anti-irritant that exceeds the activity of Cola nitida (Vent.) A.Chev. extracts.

In industry, lipase enzymes originate mostly from microbial sources and pancreatic extracts, and are used widely for hydrolysis of fats and oils. Recently industrial lipases have been identified that hydrolyze specific fatty acids. Other industrial lipases are used to form triglycerides and esters from free fatty acids and the appropriate alcohol.

Lipase preparations can be obtained from various grains and seeds (Hassanien et al. 1986. J. Am. Oil Chem. Soc., 63:893–897). Oat seeds are particularly rich in lipase. Hammond and Lee (U.S. Pat. No. 5,089,403) demonstrated that oat groats could be used to hydrolyse triglycerides. Piazza and coworkers (Piazza et al. 1989. Biotechnology Letters Vol. 11 No. 7 487–492) demonstrated that oat lipase specifically cleaved unsaturated fatty acids from tallow triglycerides when in an aqueous solution. However, in nonpolar solutions, little specificity of oat lipase prepared from whole ground oat groats was found in the hydrolysis of soybean, corn and olive oil (Piazza 1991. Biotechnology Letters Vol. 13 No. 3 173–178) and castor oil (Piazza 1991. Biotechnology Letters Vol. 13 No. 3 179–184). In Piazza's methods, 0.4 g of oil was hydrolyzed in 24–48 h using 4 g of ground groats. Although the specificity of the lipase is useful for industrial processes, oat lipase from ground groats is not sufficiently active for most industrial applications.

One preferred embodiment of the present invention describes the means to prepare an oat lipase product on solid support that has lipase activity similar to that observed for commercial enzyme preparations.

It has long been known that oat groats are relatively rich in oil when compared with other grass seeds. However, all oat oil fractions are difficult to extract and refine. Present processing techniques allow the extraction of oat oil from whole oat groats. Boczewski extracted oat oil from oat groats by admixing rolled dehulled oats with a nonpolar solvent (U.S. Pat. No. 4,220,287). Potter et al. (U.S. Pat. No. 5,620,692) describe the recovery of oil from cereal grains using hexanes or heptanes as extraction solvents. The solvent is then eliminated by evaporation, typically distillation. The resulting crude vegetable oil contains numerous fine particles consisting predominantly of proteins (20–60%). The crude oil is then subjected to various refining steps including filtration to remove particulates, water washing to remove solids and gums, acid washing to remove phosphatides, alkali neutralization to remove free fatty acids, chilling ('winterization') to remove high-melting triglycerides, decolourizing ('bleaching') with activated bleaching earth or activated carbon and deodorizing by heating under vacuum. Potter et al. claimed that oil prepared in this manner left a greasy feel on the skin and was not readily absorbed. The preferred embodiment of U.S. Pat. No. 5,620,692 to prepare oat oil involved first hexane extraction of whole oat flour followed by removal of the solvent phase. The remaining oil was heated in a jacketed tank to 70–75° C. and 3% weight of soft water was added to the oil. The oil and water were stirred for 30 minutes and then centrifuged to remove solid material. The water washing was repeated to yield a clarified oil. The oil was then dried under nitrogen at 100–105° C. The oil was finally degummed by the addition of either phosphoric or citric acid.

Oat oil has higher levels of phospholipid and free fatty acids than other oils and is difficult to refine as described above. Refining oat oil to remove fatty acids and phospholipids results in considerable product losses. We disclose methods whereby oat oil quality is improved by drying the pearlings to less than 4% moisture. Removal of water allows the endogenous oat lipase catalyst to reduce the free fatty acid level in the pearlings. This step alone greatly reduces refining losses. We also disclose that surprisingly, extraction of the pearlings with aqueous ethanol selectively removes colour impurities and phospholipids. Oat oil extracted from pearlings that have been previously extracted with aqueous ethanol, is light in colour, low in phopholipids and easily refined to a commercial product with acceptable losses.

OBJECT OF INVENTION

We have now surprisingly discovered that if up to 15% of the mass of the oat groat is first removed through an abrasion procedure, without substantially altering the shape of the oat groat, the abraded groat may then be subjected to steeping action in an aqueous environment for only 4 hours instead of 24 hours as in the prior art. The steeped groat can be wet milled in aqueous alcohol according to the prior art to yield similar bran and flour products. There is a further advantage in that it has been found that the effective aqueous alcohol concentration can be reduced from the previous 80% w/w to 50% w/w without affecting the process or the acceptability/ stability of the two principal products. Oat lipase, the enzyme most responsible for the hydrolysis of triglyceride fat present in the oat groat and responsible for the production of off flavours and odours, has been found to be inactivated at aqueous alcohol concentrations as low as 40% w/w. We have, however, found it preferable to use 50% w/w alcohol as the wet milling process fluid since, in contrast to 40%, the handling characteristics of the process mass are not negatively affected.

Bran produced in this manner is unique in that, although it has had minimal exposure to heat during preparation, any lipase activity has been eliminated as a result of employment of aqueous alcohol as a processing medium throughout the bran isolation. Further, bran prepared in this manner is also much reduced in starch content which lessens the contamination of the final product. In most laboratory preparations of linear polysaccharides, extracts are seldom exposed to mechanical shear at levels that would cause partial de-polymerization with a resultant reduction in functional viscosity. In commercial practice, such extracts must be pumped during transfers between vessels and also be centrifuged to clarify the extract from suspended solids. Frequently, high shear is encountered in such equipment which can damage the functionality of the final product. In order to minimize mechanical shear effects on the gum during extraction, the extraction is carried out at a high water to bran ratio (>60:1) and at a temperature in the range 60–100° C. We have also found it preferable to include the addition of a thermally- stable alpha amylase at the extraction step since any viscosity generated as a result of swelling of residual starch in the bran is immediately reduced and does not therefore limit the extraction of the target beta-glucan. Most of the bran residues can be separated from the liquor by a combination of screening and a de-sludging centrifuge. The hot liquor is next filtered, partially concentrated (<6:1) and then filtered a second time. The resulting solution is lightly pale straw coloured but is translucent. The gum product may be isolated from the mother liquor using known methods such as precipitation by an aliphatic alcohol, alcohol dehydration and air drying to yield a white fibrous product of purity >80%. This product develops good viscosity in water at 1% beta-glucan content and the resulting solution is near water-clear. It has preferred uses in the cosmetics sector and has potential in certain medical applications such as in wound healing.

The novelty of the beta-glucan recovery lies with the use of an oat bran containing beta-glucan in a pre-hydratated form as the preferred starting material; in the extraction of bran with heat-stable amylase instead of acids or alkalies; in the use of a double filtration step to remove impurities and improve the quality and functionality of the beta-glucan final product.

We have further observed that the flour produced from this reduced-time process is well suited to subsequent fractionation into starch and protein, without the added inconvenience of having to be concerned about the removal of large amounts of bran, since most of the bran has been removed through a combination of dry abrasive pre-milling and wet processing of the groat in aqueous alcohol. From an economic perspective, the yield of starch and protein per unit weight input of de-branned material is substantially higher. These newer developments are seen in terms of reduced overall processing costs.

We have found that oil, lipase and anti-irritant fraction are concentrated in the surface layers of dehulled seeds from the genus Avena. The outer 15% of the grain contains half of the seed oil, all of the lipase and half of the anti-irritant activity present in the whole seed. These surface layers can be obtained in commercial quantities by surface milling the dehulled grain using commercially available equipment. The process of first removing the outer layers of the seed, sequentially extracting these layers with aqueous ethanol and hexane, and drying the extracts yields a highly concentrated anti-irritant (which reduces skin reddening by 70 to 90%) and a high quality oil that is easily refined. The proposed method is the most efficient method known for obtaining a highly active anti-irritant fraction and a refined oil from oat.

Once the outer layers of the oat seed are removed from the groat there is a tendency of the oil to lose quality due to the hydrolysis of the glycerides by oat lipase. It is not uncommon for fatty acid levels to increase to as high as 70% in stored groat pearlings. However, as part of the preferred method it is possible to improve the quality of the oat oil obtained from the pearled fraction even after the fatty acid levels have increased to unacceptable levels. This improvement is achieved by drying the pearlings in a fluid bed dryer. The drying treatment removes water and under very dry conditions lipase is capable of catalyzing the reversion of free fatty acids to glycerides. The oil is then readily removed from the pearlings using a nonpolar solvent like hexane. The process of first improving the oil quality, then removing the oil results in a high quality oil with low fatty acid levels. This process also produces a highly stable lipase-active powder which approaches the activity of commercial lipase powders derived from fungal sources. The proposed method is the most efficient method known for obtaining a highly stable lipase-active powder and a high quality oil from oats. The oat oil produced by hexane extraction of the dried pearlings has the added characteristics of being rich in UV absorbing compounds and the anti-microbial protein avenothionin.

BRIEF DESCRIPTION OF INVENTION

By one aspect of this invention there is provided a process for producing oat pearlings, oat flour and oat bran products from oat groats, comprising: surface abrading said oat groats so as to remove up to about 15% by weight of said oat groat without substantially altering the shape thereof, separating said oat pearlings from said abraded oat groats, steeping said separated oat groats in an aqueous medium for up to about 4 hours at a temperature up to about 50° C., separating said steeped groats from said aqueous medium, and wet milling said steeped groats in an aqueous alcoholic medium, containing up to about 50% of an aliphatic alcohol, so as to produce a slurry, separating said aqueous alcoholic slurry into an insoluble oat bran product and a soluble endospermic product, and recovering said oat flour from said soluble endospermic product.

By another aspect of this invention there is provided a process for producing an anti-irritant product and a light oat oil product from oat pearlings, comprising: extracting said pearlings with a volatile aqueous polar solvent and recovering said anti-irritant from said extract; drying said extracted pearlings and re-extracting with a nonpolar solvent to recover a light oat oil.

By another aspect of this invention there is provided a process for producing an anti-irritant product from oat pearlings, comprising: extracting said pearlings with a nonvolatile polar solvent, e.g. propylene or butylene glycol, and recovering said anti-irritant from said extract.

By another aspect of this invention there is provided a process for producing lipase and a dark oat oil product from oat pearlings, comprising: extracting said pearlings with a nonpolar organic solvent and recovering dark oat oil from said extract; and drying said extracted pearlings to yield a lipase active product.

By yet another aspect of this invention there is provided a process for producing an enriched oat bran and a refined oat flour from pearled oat groats comprising: steeping said pearled oat groats in an aqueous medium for up to about 4 hours at a temperature up to about 50° C., separating said steeped groats from said aqueous medium, and wet milling said steeped groats in an aqueous alcoholic medium, containing up to about 80% of an aliphatic alcohol, so as to produce a slurry, separating said aqueous alcoholic slurry into an insoluble oat bran product and a soluble endospermic product, and recovering said oat flour from said soluble endospermic product.

By yet another aspect of this invention there is provided a process for producing beta- glucan from an insoluble oat bran product comprising: extracting said insoluble oat bran product in an aqueous slurry having a water to bran ratio of at least 60:1 at a temperature in the range 60–100° C., in the presence of alpha-amylase; separating said slurry to recover a beta glucan containing liquor; and concentrating, filtering and precipitating beta-glucan from said liquor.

By yet other aspects of this invention there are provided products produced by the processes outlined herein above.

DETAILED DESCRIPTION OF PREFERRED EMBODIMENTS

Oat groats

Figure 1:
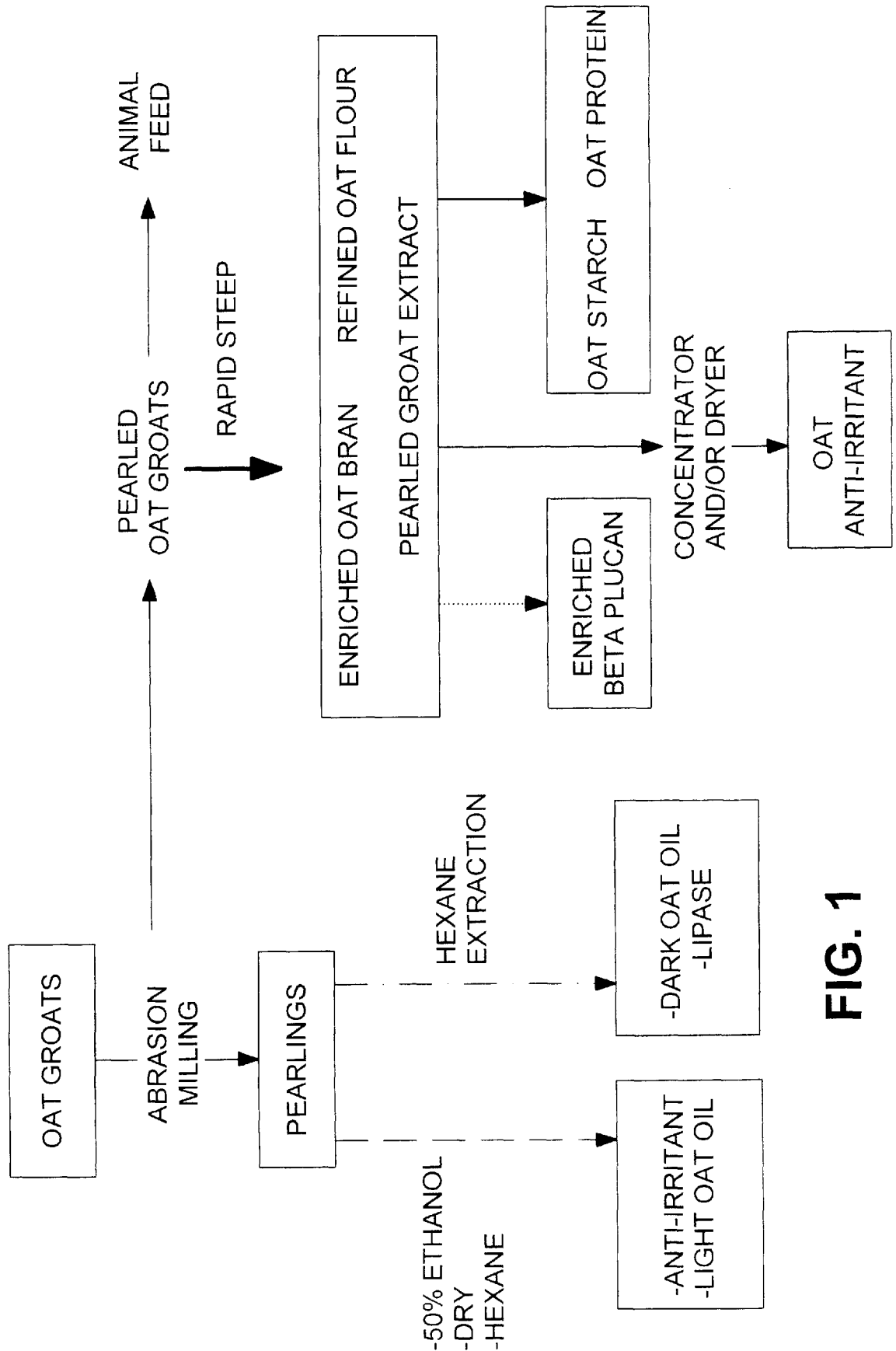
FIG. 1. is a schematic flow diagram illustrating aspects of the present invention.

Oat may be purchased either with the hull attached or as a de-hulled groat or as a hull-less oat. Hulls may easily be removed by techniques known to those skilled in the art, e.g. with an impact dehuller. Any broken fragments of groats can be removed from the sound groats by a simple process of passage over an inclined plane gravity table.

In this embodiment the sound groats are next subjected to a surface abrasion such as may be accomplished by rubbing the groats between a Carborundum® rotating roller against a static screen. The fine pearlings thus removed pass through the screen and the groats are retained in a substantially whole manner. The surface-abraded groats are then steeped in water at 45–50° C. as described in our previous inventions (Burrows et al., 1984 and Collins and Paton, 1992 supra) but the steeping time is no greater than 4 h. The steeped groats have now imbibed approximately their own weight in water and are removed from the remaining steep water by straining or draining. Groats are then slurried in a mixture of an aliphatic alcohol, e.g. ethanol, at an effective alcohol concentration of 50% w/w and passed continuously through an in-line macerator to wet-mill the groats. The bran is first removed by screening by any of several options known to those skilled in the art. We have found it most convenient to use a parabolic screen with a sieve opening of approximately 200 microns. The separated bran is removed to a second vessel, mixed with fresh 50% alcohol and washed by re-processing over the parabolic screen. The washed bran may then be de-liquored by any known technique such as through the use of a pressure filter, continuous roller press, basket centrifuge or a decanter centrifuge or the like, and then dried using any one of several conventional means.

The under slurry from the de-branning procedure is further screened on a second parabolic screen with a mesh opening size of 50 microns to remove very fine bran particles. The under flow, containing the endospermic flour, is next centrifuged and the alcohol-wet flour mass may either be recovered by drying or optionally further fractionated into starch and protein by any of the methods known to those skilled in the art. Typically, fresh water is added and the slurry is adjusted to pH 9.0 using sodium carbonate to avoid any incipient gelatinization of the starch which might occur if stronger alkalies were used. After stirring in an appropriate vessel at a temperature no greater than 50° C. for 1 hour, the slurry is differentially centrifuged to produce a liquor which predominantly contains the protein at the expense of starch.

The protein liquor is then neutralized using any one of several food-grade mineral acids and may be concentrated by any means known to those skilled in the art and dried to yield a dry protein concentrate.

The crude starch liquor may next be re-processed by washing and centrifugation to remove contaminating protein. The washed starch liquor is then neutralized, further washed to reduce the salt content, concentrated and dried.

Most botanical and cereal chemistry texts routinely describe starches in terms of their granule size distribution. Since not all starches have the same distribution of sizes, this knowledge is often useful when deciding upon potential end uses for a starch product, especially if the product is to be used in a dried form. Unfortunately most particle size distributions are determined as a wet aqueous slurry being caused to pass a beam of light. Thus any starch that, in the dry state and arising from commercial processing, is in an aggregated form, will automatically disintegrate in water and the distribution profile will be one that falsely describes the true particle size of the starting dry material. This discrepancy can be quickly verified by repeating the aqueous slurry determination but in an non-aqueous solvent which will not cause the starch particles to disintegrate.

Typically, we have found that oat starch from a commercial dryer is very coarse to the touch, is highly aggregated and is quite unsuited for most intended dry end uses. We have found it convenient to mill the dried product using a counter-rotating pin mill and recover the product from the cyclone separator of this apparatus. Surprisingly, we have noted that such treatment results in a fine powdered oat starch of mean particle size in the range 7–9 microns, which does not exhibit any physical granule damage and which possesses a touch and feel quite similar to talc, a substance widely used in the cosmetics and personal care products as a dusting powder.

EXAMPLE 1

Small Scale Fractionation of Abraded Oat Groats 150 g of dehulled or hull-less oat groats were surface abraded in a laboratory Satake mill, fitted with a #30 stone and a 1.00 mm slotted screen until no greater than 10% of the groat weight had been removed. The abraded groats were then steeped in water containing 0.1% sodium metabisulphite at 50° C. for 4 hours during which the groats rapidly imbibed water to the extent of their own weight. The excess water was poured off and the swollen groats were next wet milled in a laboratory blender at an effective alcohol concentration of 50%. The milled slurry was passed over a 200 micron screen to separate the course bran as discreet pieces; this bran was washed with 50% alcohol, rescreened and air dried to yield an oat bran which contained 14–20% beta-glucan, by analysis, depending upon the variety of oat selected.

The stream passing the 200 micron screen was then screened over a 50 micron screen to remove the small quantity of bran fines remaining in the liquor. The light cream coloured liquor contains the endospermic flour which may be recovered by any centrifugal means known to those skilled in the art, washed with aqueous alcohol and air dried. Alternatively, the centrifuged heavy solids were slurried in water, the pH was adjusted to 9.0–10.0 using 20% sodium carbonate solution to prevent chemical swelling of the starch granules, and the slurry heated to 45° C. for 1 h with stirring to extract the protein. On centrifugation, the starch sedimented as a white layer at the bottom of the centrifuge bottle; immediately above the starch layer was a brown semi-solid layer consisting mainly of protein and a thinner top layer. The two upper layers were removed to a separate vessel, the pH adjusted to 6.5–7.0 and the contents freeze dried. The product was found to have a protein content in the 60–65% range by analysis. The heavy starch layer was resuspended in water and again centrifuged to remove protein impurities. The wet starch was then conveniently recovered in the laboratory by washing first with alcohol followed by a final wash with acetone and air dried. Starch produced in this manner had a protein content of <0.5%.

EXAMPLE 2

Large Scale Fractionation of Abraded Oat Groats

Oat groats, free of residual hulls and any dehulled oat, were passed through a small pilot scale abrasion mill (Satake Industries USA) using a # 36 grit stone and a 1.2 mm slotted screen. From considering the micro-structure of the oat groat (Fulcher and Miller, 1992) and from pre-tests conducted on this mill, the settings of the feed rate opening, the discharge weight opening and the resistance bar on the screen were adjusted to remove <8% of the groat weight as pearlings. Higher levels of pearlings removal lead to an undesirable increase of beta-glucan in the pearlings, a resulting loss in yield and beta-glucan content of the wet processed bran and an increase in steeping difficulties due to excessive water absorption.

Seven hundred kilograms of abraded groats were steeped in 2000 kg of soft water, containing 0.03% sodium metabisulfite, at 500° C. for 4 h. The steep tank was drained and the steeped groats, 1600 kg, were flushed out of the tank in a stream of aqueous ethanol such that the effective concentration, allowing for the imbibed water in the groats, was 50% w/w. The tank contents were pumped sequentially through a pair of in-line disintegrators, the first fitted with an extra coarse head while the second one contained a parallel arrangement of a coarse, medium and fine head. The resulting slurry was pumped through a parabolic screen (200 microns) to remove the majority of the bran as a coarse impure fraction while the underflow stream was collected in a separate tank. The coarse impure bran was washed with fresh 50% alcohol, re-screened and the underflow combined with the first. The washed coarse bran was processed through a basket centrifuge and dried using a fluid bed dryer to yield 92 kg of oat bran. This oat bran is recovered mainly in a flake form which is found to exhibit similar water absorption characteristics to that described in our previous patent (Collins and Paton, 1992 supra).

The underflow containing the flour was pumped through a second parabolic screen (50 micron) to remove bran fines which were washed and processed as described for the coarse bran. Thirty-three kilograms of the dried fine bran product was recovered.

The completely de-branned flour slurry was fed to a horizontal decanter centrifuge to remove the bulk of the liquor from the wet flour solids. If desired, the latter were dried to produce a dry flour. Optionally, the wet flour solids were slurried in soft water, the pH adjusted to 9.5 using a 20% concentrated solution of sodium carbonate and the slurry stirred at 40° C. for 1 h to extract the protein. The slurry was passed through a nozzle bowl centrifuge to produce a heavy phase (starch) and light phase (protein). The latter was adjusted to neutrality with 4N HCl stock solution, concentrated in a flash evaporator and spray dried to produce a protein concentrate (62.4% protein) in powdered form. The heavy phase was washed twice counter-currently with fresh water and once again following a neutralisation step, to produce a thickened prime starch slurry which was subsequently dried in a stream of circulating hot air on a ring dryer to yield a prime starch of protein content <0.5%. The starch washings could be pooled, centrifugally thickened and the solids recovered as a secondary impure starch.

The prime starch cake was then subjected to a double milling using a counter rotating pin mill to produce a product with a mean particle size of 8.1 microns in which there was no evidence of granule starch damage as a result of the pin milling procedure.

The aqueous ethanolic extract from the initial wet milling of the steeped groats was collected and filtered on a plate and frame filter press to remove any small amount of suspended solids and then concentrated to recover the bulk of the alcohol. The resulting liquid concentrate was optionally spray dried to give a powdered solids preparation; alternatively, the liquid concentrate was mixed with an equal volume of a water miscible food grade glycol, e.g. propylene or butylene glycol, where such extracts find utility in the cosmetics, personal care and animal health care sectors as an anti-irritant.

EXAMPLE 3

Laboratory Preparation of Beta-glucan from Oat Bran

Ten grams of a high (>14%) beta-glucan containing oat bran were slurried in 800 mL of water (80–90° C.) and stirred for 1 h to re-hydrate the gum. Two hundred and fifty Units of an alpha-amylase preparation (Type X11A-Sigma Chemical Co., St. Louis, Mo.) were added and the extraction was continued for a second 1 h period. The slurry was screened through an 8XX bolting cloth to remove most of the course bran which was returned to the beaker for a second extraction with an additional 400 mL of water. The combined liquid extracts were heated to 80–85° C., 0.5 g activated carbon and 5 g of Celite added, and the solution stirred at this temperature for 30 min. This slurry was filtered under vacuum through a bed of Celite to remove most of the fine suspended impurities. The resulting liquid was reduced in volume in a rotary evaporator to ⅕–⅙ of the original. The concentrate, at a temperature of 85–90° C., was re-filtered through a second bed of Celite. The filtered beta-glucan containing extract was a pale, translucent straw colour. The temperature of the filtrate dropped to 60–65° C. throughout these steps. An equal volume of ethanol or isopropyl alcohol was then added with stirring to precipitate the gum as a whitish-translucent gel mass. The precipitated beta-glucan was removed by screening on 8XX bolting cloth, washed and dehydrated with 95% alcohol. The alcohol-wet gum was air dried to give the final product as a white powder of 84% beta-glucan content.

EXAMPLE 4

Large Scale Preparation of Beta-glucan from Oat Bran

Twenty-five kilograms of a high (>14%) beta-glucan oat bran flake was mixed with 2000 L of water at 85° C. and stirred for 1 h. A commercial source of heat stable alpha-amylase was added and the slurry was held for a further 1 h to convert the gelatinized residual starch into lower saccharides, as evidenced by the absence of the blue-black color in a starch-iodine test. After screening the tank contents through a 45 micron screen, 500 L of cold water was added to the ensuing liquid phase to reduce the tank temperature to around 65° C. and provide an extraction ratio of 100:1. The extract was pumped through a de-sludging centrifuge to remove coarse material and then filtered on a filter press pre-coated with Celite. The extract was then concentrated 5:1 and precipitated with an equal amount of alcohol. The swollen gum was skimmed off and triturated several times with alcohol to progressively remove water. The final product was recovered first on a basket centrifuge and dried in a vacuum tray dryer to yield 1.44 kg of beta-glucan powder. This product analysed at 74% beta-glucan content; 8.4% protein; 0.38% fat and 2.18% ash.

The viscosity behaviour of a 1% solution of this gum (based on its beta-glucan content) was compared with a 1% solution of Hyalucare(TM), a commercial hyaluronic acid preparation in use by the cosmetics industries. The Consistency Index was 14.5 Pa.S and 16.9 Pa.S and the flow index was 0.346 and 0.268 respectively, for the oat gum and hyaluronic acid. A beta-glucan of purity >74% could be obtained by re-filtering the 5:1 liquid concentrate to further remove impurities prior to the gum being precipitated with alcohol. The resultant gum product had a higher beta-glucan content (typically in excess of 80%), and when re-dissolved in water gave water-clear solutions suitable for cosmetics or medical applications.

Oat pearlings

Our invention also relates to the development of commercial surface milling to produce fractions from oat that are specifically enriched in lipase, oat oil and anti-irritant. The fractionation procedure includes a simple mechanical milling step that removes the outer 1–15 percent of the oat groat. This pearled fraction contains virtually all of the lipase activity, half of the anti-irritant activity and half of the oil of the whole seed. The pearling process yields a fine powder that through subsequent processing, can be extracted to produce lipase, oat oil and oat based anti-irritant fractions. In a preferred implementation of this invention performed on oat groats, the pearlings contain five times the lipase activity and three to four times the oil content of the whole groat. The anti-irritant derived from the pearlings is twice as effective as an anti-irritant derived from whole oat groats.

Recovery of oat seed oil and lipase

Oat pearlings have a high level of both lipase activity and oil. The oat oil is a substrate for the lipase and, in the presence of moisture, is continuously degraded from a product which is mostly triglyceride to a product which is mostly fatty acids. Oat oil is difficult to refine and refining losses are increased by high levels of fatty acids. Lipase can be inactivated to stabilize oat bran and limit the production of free fatty acids from oat oil but inactivation of the lipase makes it impossible to obtain any commercial value from the oat lipase. As a unique part of this disclosure it was found that removal of water from oat pearlings to less than four percent using a suitable commercial dryer did not inactivate the lipase while preventing the formation of free fatty acids. Moreover, we found that drying oat pearlings that had high fatty acid contents surprisingly resulted in the catalytic reversion of fatty acids to glycerides through the action of endogenous lipase in the oat pearlings. The oat oil extracted from pearlings remediated by drying to low moisture contents was found to be more easily extracted in higher yields and more easily refined than oil extracted from pearlings that were not remediated.

Pearlings treated by removal of moisture at temperatures from 30 to 80° C. could be extracted with nonpolar organic solvents such as dry isopropanol, hexane, heptane, acetone, ethyl acetate etc., to yield a darkly coloured oil and an oil free pearlings fraction. The defatted pearling fraction was found to contain a highly active heat stable oat lipase that could exhibit as much as six times the activity of whole oat groat fractions.

Recovery of oat oil and anti-irritant fraction

In the present invention oat pearlings may also be extracted with a mixture of polar solvents such as ethanol, propanol or methanol with water or a glycol (glycerol, propylene glycol). The extraction process removes approximately three to fifteen percent of the weight of the pearlings. The extract solution may then be dried by a combination of evaporation and spray drying treatments and depending upon the solvent used for extraction, the process will yield a powder or viscous solution. The dried extract may be utilized directly as a highly potent anti-irritant in cosmetic and toiletry applications. The extracted solids can then be dried and further extracted with a nonpolar solvent such as hexane, heptane, acetone or ethyl acetate. The nonpolar solvent extracts a high quality clear yellow oat oil that is low in phospholipids and fatty acids.

EXAMPLE 5

Yield of Ethanol Extracts

Twenty batches of Calibre groats were milled in lots of 200 g in a Satake laboratory mill (#36 stone 1 mm slot width) for 30 s and the pearlings and pearled groats separated. The mill was operated without cleaning between batches so as to simulate continuous performance. Yields of pearlings and pearled groats from this treatment are shown in Table 1 under first milling. The pearled groats from the first milling were pooled and divided into 200 g lots and milled for an additional 30 s and the pearlings and twice milled groats separated. The twice pearled groats were pooled, divided into 200 g lots, milled a third time and the pearlings and thrice pearled groats were separated. The yields of pearlings and pearled groats from the second and third milling are given in Table 1 under the headings second milling and third milling respectively.

The efficiency of ethanol extraction on pearlings and pearled groats was determined. For each fraction 100 g was ground in 300 g of aqueous ethanol (50:50 w:w) in a Waring blender for 1 minute. The ground sample was stirred in the alcohol solution in a beaker for 20 minutes. The solution was filtered over a 40 mesh screen and the filtrate was saved. The solids were resuspended in an additional 300 g of aqueous ethanol (50:50 w:w), stirred in a beaker for another 20 minutes and filtered as before. The filtrates were combined and the solids were discarded. The filtrate was settled for one hour and the clear supernatant transferred to centrifuge bottles and centrifuged at 2,000×g for 15 m. The remaining solids were discarded.

The extracts were treated with Dow antifoam at a rate of 3 ppm and evaporated at 70° C. to remove ethanol. Additional ethanol was periodically added to the flask to increase the rate of water removal. Once the material was brought to dryness each flask was then reweighed to determine the yield of dry solids from each extraction. This data is listed in Table 2 as the weight of the evaporate. The dry material in the flask was a gummy solid. The samples were then removed from the flask and transferred to a pestle and ground with a mortar. During grinding, the gummy matter became brittle and was converted by the process to a finely divided powder. The ground sample was placed in a beaker and stirred in 95% ethanol for 30 minutes, then filtered and rewashed with 95% ethanol. The retained solids were dried on a watch glass and weighed (Table 2).

EXAMPLE 6

Anti-irritant Activity of Pearlings Extract

Two thousand kilograms of Calibre groats were passed through a modified Satake Model KB20g rice polishing mill. The mill was operated with the feed gate at maximum opening (position 4.5), pearled product outlet resistance weights at minimum (position 9 smallest weights) and internal resistance bars set at position 5 on both sides. The mill was modified by the addition of a sheet metal gate that divided the first one third segment of the mill from the next two thirds. The choice of the modification was made due to the observation that the first third of the mill removed primarily oat seed hairs while the remainder of the mill removed other materials. Milling generated 35 kg of the first pearled fraction (1 pearlings) and 65 kg of the second pearled fraction (2 pearlings). In subsequent processing these pearlings were either blended to yield a combined fraction or processed individually.

A sample of 1+2 pearlings (637 g) in the ratio in which these were obtained, was extracted in 4× weight (2,548 g) of aqueous alcohol solution (50:50 H2O:ethanol w:w) by placing the sample in a beaker with an overhead stirrer. Samples of 500 mL were removed from the beaker after 5 min, 1, 2, and 24 hours. Samples were removed during agitation so that solids to liquids ratio remained constant during extraction. The efficiency of this extraction and the anti-irritant activity of the extracts are given in Table 3. Samples are identified in the table by the length of extraction.

A sample (97 g) of 1 pearlings was extracted with 3× weight of aqueous alcohol solution (50:50 H2O:ethanol w:w) for 18 hours by placing the sample in a beaker with an overhead stirrer. The efficiency of this extraction and the anti-irritant activity of the extract are given in Table 3.

A sample of 1+2 pearlings (637 g) was extracted in 4× weight (2,548 g) of aqueous alcohol solution (50:50 H2O:ethanol w:w) by placing the sample in a beaker with an overhead stirrer for 24 hours. The solids were allowed to settle and the ethanol was decanted from the solids leaving a sludge. Two hundred grams of the extracted pearlings sludge was extracted for a further 4 hours in 2× weight (400 g) of aqueous alcohol solution (50:50 H2O:ethanol w:w) by placing the sample in a beaker with an overhead stirrer. The efficiency of this extraction and the anti-irritant activity of the extract are given in Table 3.

Each sample was centrifuged at 2000× g for 15 min and the supernatant was decanted. For samples in the time study, the weight of the supernatant and of the air dried pellets was recorded. Ethanol extracts were brought to dryness as described in Example 5.

Measurement of anti-irritant activity

Upon application to the skin, a prepared solution of the anti-irritant fraction is effective in reducing adverse reactions of the skin to a number of chemical irritants. For example, when a composition containing 2% of the anti-irritant fraction, prepared as described above, was applied by a panel of persons (who were chosen because of their sensitivity to a variety of irritant compounds) just before the persons applied to their skin a known irritant (Balsam of Peru), the irritation response of the panel to the irritant was significantly reduced (Table 3).

Preferably, the anti-irritant fraction is applied to the skin before or after (about 30 minutes before or less, preferably 15 minutes or less) a cosmetic or pharmaceutical composition containing a chemical irritant. The composition may also be blended with the chemical irritant thereby permitting simultaneous application of the extract and the irritant.

EXAMPLE 7

Lipase Activity

Measurement of lipase activity

Prior to lipase assays it is necessary to remove oil and fatty acids from the sample to reduce background interference. In preparation for assay, pearling samples are first solvent extracted with hexane in a Soxhlet for 6 h and the extracted samples allowed to air dry in a fume hood overnight. This treatment reduces sample oil content to acceptable levels. The samples then are mixed and approximately/exactly 0.50 g of sample is weighed into a 15 mL Corex centrifuge tube. 5.0 ml of acetone, (chilled in a −20° C. freezer for 15 minutes) and 0.6 ml of acetate solution (50 mM acetic acid, adjusted to pH 3.0 with NaOH) is added to the tube.

The tube is vortexed three times at five minute intervals and then centrifuged at 9428× g using a Sorvall HS-4 swinging bucket centrifuge head. The solution is decanted and discarded. The addition of acetone and successive centrifugation is repeated three times. The sample is air dried overnight. The sample is essentially free from fatty acid contamination after this washing treatment.

Assay Procedure

To each tube containing the active enzyme sample, 1.0 mL of the following reagent mixture is added: 2.0 g Triton, 0.8855 g triolein and 0.2 g benzene, mixed with 0.6057 g Tris-HCl (pH 7.6). Tubes are vortexed and incubated in a 370C water bath for 2 h. The reaction in the active tube is stopped by the addition of 5 drops of 6.0 N HCl followed by vortexing. To each tube 5.0 mL of chloroform:hexane:methanol (CHM:49:49:2) is added. The tube is vortexed 3 times at five minute intervals and centrifuged as before. The solution is decanted into 25 mL graduated cylinders. The addition of solvent and successive centrifugation are repeated 3 times, the supernatant pooled and made up to 20 mL in the graduated cylinder and vortexed. One mL is removed for colorimetry determination based on the method of Shipe et al. (1980. J Dairy Sci. 63:193–198). To provide blank samples used in the calorimetric determination the enzyme is inactivated by the addition of 0.25 mL 6.0 N HCl to the reagent mixture. The blank sample is then treated as described above.

Available commercial varieties of oat grown in Canada were assayed as described above for lipase activity to determine the most effective source of lipase (Table 4). In all cases the lipase activity of ground whole groats was approximately 20–25% of the activity of the pearlings of the whole groats. The most active lipase sample was obtained from the pearlings obtained from seeds of the oat variety Calibre. This variety produced a powdered lipase extract that exhibited over 36% of the activity of commercially available liquid lipases and over 47% of the activity observed for a stabilized powdered lipase.

The lipase powder from oat was found to be effective in hydrolysing a number of lipids as shown in Table 5. The activity for hydrolysis of rapeseed oil was half that observed for most other oils, suggesting a low specificity of the enzyme for erucic acid. Lipase powders were also tested for their long term stability. It was found that lipase activity could be maintained for two years in storage at room temperature without loss if the pearlings were stored dry and defatted by organic solvent extraction where the organic solvent was hexane, acetone, diethyl ether or other suitable organic solvent. The pearlings maintained lipase activity even when heated to 80° C. for several hours. Inactivation required heat treatments of over 100° C.

EXAMPLE 8

Stabilizing and Improving Oil In Oat Pearlings.

Pearlings, prepared as described in example 5, were immediately stored in a freezer at −20° C. until required. Sequentially, ten kg of first and second pearling fractions were placed in a fluid bed dryer and dried to less than 4% moisture to limit free fatty acid production by lipase hydrolysis of glycerides. The dryer was set at 20 psi air pressure, 80° C. with the damper 25–33% open. The dryer was operated for 1 h after the exit temperature reached 70° C. The pearlings were stored in a sealed plastic pail at 0° C. A further 10 kg of first and second pearled fractions was placed in an autoclave at 121° C. for 1 h to inactivate lipase. Pearlings produced by each of the three treatments were extracted with a 10 liter lass Soxhlet using hexane as a solvent. The hexane was removed using a 20 L rotary evaporator and the fatty acid content of the oil from the three oat pearlings was determined. The oil recovery of all three treatments was similar, i.e. approximately 15% of the weight of the pearlings. The oil from pearlings that were not treated after milling had a fatty acid content of 40% while the autoclave treatment increased the fatty acid level to 70%. Surprisingly, heating the oat groats in a stream of dry air reduced the fatty acid content of the oil from 40% to 27% of the oil weight. The lipase in the oat groats had sufficient activity to form oat oil glycerides from fatty acids and partial glycerides if water was removed from the system.

EXAMPLE 9

Extraction of Oat Oil With Commercial Equipment

Pearlings (22.7 kg) were blended with 91.7 kg of hexane with agitation for 30 minutes. The stirred slurry was transferred to a basket centrifuge lined with a 25 micron bag. The output filtrate from the basket centrifuge (59.0 kg) was recovered. The solid retentate in the basket centrifuge was slurried with an additional 72.3 kg of hexane and stirred for an additional 30 minutes. After 30 minutes the slurry was again passed through the basket centrifuge. An additional 66.0 kg of filtrate was recovered from the centrifuge.

The hexane extracts were combined and concentrated using a continuous thin film evaporator under constant vacuum (−74 kPa) operated at 1.75 kg/min feed rate at 50° C. A total of 3.4 kg of oat oil was recovered or approximately 15.0 percent of the weight of the pearlings, and analysed, the results being tabulated in Table 5.

EXAMPLE 10

Effect of Liquid/Solids Ratio on Single Stage Aqueous Ethanol Extraction of Pearlings Oat pearlings derived as described in example 5 were extracted either with a single stage or a multiple stage extraction protocol. In the single stage extraction, a mixture of ethanol and water (1:1 w:w) was added to the pearlings to determine total extraction of solids. The total volume of solvent used was varied from 40 to 120 mL while the total weight of pearlings was held constant at 20 g. It was found that the recovery of solutes increased with the amount of solvent added but that the concentration of solutes in the solvent decreased (Table 6).

EXAMPLE 11

Counter Current Extraction of Pearlings With Aqueous Ethanol

Counter current extraction allows the removal of solutes without excessive dilution of the product. Counter current extraction of oat pearlings was achieved by contacting 20 g of oat pearlings three times with 40 mL of aqueous ethanol (1:1 w:w). The aqueous ethanol was then used to contact a second and third batch of oat pearlings. The supernatant from the second and third batches of pearlings were used in a similar fashion to extract subsequent batches of pearlings. Four solid fractions of oat pearlings were extracted three times each in a counter current protocol. The extraction mixtures were stirred for either 5 or 25 minutes between extractions to determine the most efficient extraction time. Supernatant and solids were separated by centrifugation for 5 minutes at 1,000× g. Table 7 shows the relative efficiency of extraction expressed as % recovery, using 3 stages of counter current extraction with a 5 min stirring while Tables 8 and 9 show the results of a similar extraction performed with a 25 min extraction interval. The counter current extraction exceeds the efficiency of extraction achieved by a single stage extraction in two ways. First, counter-current extraction produces a highly concentrated extracted solution. With a solute concentration of 4–5% dry matter the counter current extraction produces a solution of similar concentration to a single stage extraction of 20 g of pearlings with 40 mL of solution (Table 6). A single stage extraction with 40 ml of solution only removed 4% of the weight of the pearlings while counter current extraction removed between 7.7 and 9.8% of the weight of the pearlings. A single stage of extraction with 120 mL only removed 6.4% of the weight of the pearlings. Therefore, counter current extraction will produce more extract with less need for pearlings and evaporation than a comparable single stage extraction protocol.

TABLE 1

Milling of Calibre groats with a Satake rice mill. Results of first 10 samples.

| | First milling | | | Second milling | | | Third milling | | |
|---|---|---|---|---|---|---|---|---|---|
| Sample # | Sample Weight (g) | Weight of pearling (g) | Weight of groats (g) | Sample Weight (g) | Weight of pearling (g) | Weight of grouts (g) | Sample Weight (g) | Weight of pearling (g) | Weight of groats (g) |
| 1 | 200 | 13.00 | 151.00 | 200 | 16.70 | 161.30 | 200 | 16.07 | 176.60 |
| 2 | 200 | 14.04 | 190.21 | 200 | 39.06 | 160.50 | 200 | 8.08 | 184.68 |
| 3 | 200 | 10.42 | 190.37 | 200 | 23.20 | 178.20 | 200 | 8.87 | 185.43 |
| 4 | 200 | 12.03 | 187.89 | 200 | 22.53 | 174.72 | 200 | 8.16 | 189.50 |
| 5 | 200 | 11.73 | 187.30 | 200 | 18.97 | 180.80 | 200 | 9.33 | 184.79 |
| 6 | 200 | 10.76 | 190.2 | 200 | 21.54 | 179.83 | 200 | 7.91 | 192.95 |
| 7 | 200 | 10.40 | 189.09 | 200 | 21.96 | 179.49 | 200 | 7.22 | 183.51 |
| 8 | 200 | 10.16 | 187.75 | 200 | 19.02 | 183.07 | 200 | 2.55 | 191.85 |
| 9 | 200 | 11.26 | 191.31 | 200 | 18.10 | 183.07 | 167.69 | 3.62 | 156.50 |
| 10 | 200 | 9.60 | 188.68 | 200 | 16.10 | 178.45 | | | |
| sum | 2000 | 113.4 | 1854 | 2000 | 217.18 | 1759 | 1767.7 | 71.81 | 1646 |
| percent | 100 | 5.7 | 92.7 | 100 | 10.9 | 88.0 | 100 | 4.1 | 93.1 |

TABLE 2

Yield of aqueous ethanol extracts of pearled oat fractions

| Fraction | Weight of evaporate (g) | Weight of product (g) | Yield of product (g) |
|---|---|---|---|
| Unmilled groats | 3.85 | 2.50 | 1.3 |
| Milled 1 x | 5.03 | 2.58 | 2.6 |
| Milled 2 x | 4.86 | 3.01 | 3.0 |
| Milled 3 x | 5.64 | 2.74 | 2.7 |
| First pearlings | 12.06 | 4.01 | 4.0 |
| Second pearlings | 7.32 | 3.83 | 3.8 |
| Third pearlings | 6.36 | 4.09 | 4.1 |
| Mixed first and second pearlings | 7.53 | 5.56 | 5.6 |

TABLE 2-continued

Yield of aqueous ethanol extracts of pearled oat fractions

| Fraction | Weight of evaporate (g) | Weight of product (g) | Yield of product (g) |
|---|---|---|---|
| Mixed pearlings | 7.22 | 4.81 | 4.8 |

TABLE 3

Yield and anti-irritant activity of aqueous extracts of oat pearlings

| Sample Extraction | Weight of evaporate (g) | Weight of product (g) | Anti-irritant activity† |
|---|---|---|---|
| 5 min | 9.82 | 4.30 | 44 |
| 1 hour | 8.01 | 4.58 | 39 |
| 2 hour | 7.51 | 5.07 | 61 |
| 24 hour | 7.80 | 5.86 | 64 |
| 1 Pearlings | 6.75 | 4.38 | 19 |
| Re-extraction | 2.31 | 1.31 | 57 |
| Commercial anti-irritant* | | | 60 |

†measured by % reduction in redness after application of Balsam of Peru
*Extract of Cola nitida (Vent.)A.Chev.

TABLE 4

Lipase activity of oat groats and groat pearlings

| Lipase sample | Activity (micromole/g.d.wt/h) | Percent of commercial lipase activity |
|---|---|---|
| Tibor groats | 14.8 | 5.4 |
| Tibor pearlings | 66.6 | 24.4 |
| Calibre pearlings | 98.5 | 36.2 |
| Cascade pearlings | 35.7 | 13.1 |
| Derby pearlings | 36.0 | 13.2 |
| Jasper pearlings | 48.3 | 17.8 |
| Robert pearlings | 83.5 | 30.7 |
| Wild Oat Avena fatua pearlings | 29.3 | 10.7 |
| Powder commercial lipase | 208.6 | 77.7 |
| Liquid commercial lipase | 272.1 | 100 |

TABLE 5

Activity of oat pearling lipase extract on various substrates

| Substrate | Activity (micromoles/g.d.wt/h) |
|---|---|
| Triolein | 42.4 |
| Borage oil | 35.2 |
| Canola oil | 36.3 |
| Sunflower oil | 43.2 |
| Rapeseed oil | 19.1 |
| Fish oil | 36.6 |
| Palm oil | 41.0 |

TABLE 6

Single stage extraction of oat pearlings

| Sample | Wet Weight (g) | Dry Weight (g) | % recovery |
|---|---|---|---|
| Supernatant 40 ml | 19.09 | 0.79 | 4.0 |
| Solids 40 ml | 37.56 | 19.01 | |
| Supernatant 60 ml | 35.10 | 1.00 | 5.0 |
| Solids 60 ml | 39.25 | 18.80 | |

TABLE 6-continued

Single stage extraction of oat pearlings

| Sample | Wet Weight (g) | Dry Weight (g) | % recovery |
|---|---|---|---|
| Supernatant 80 ml | 51.88 | 1.15 | 5.8 |
| Solids 80 ml | 40.12 | 18.80 | |
| Supernatant 100 ml | 66.95 | 1.21 | 6.1 |
| Solids 100 ml | 46.56 | 19.68 | |
| Supernatant 120 ml | 84.00 | 1.28 | 6.4 |
| Solids 120 ml | 49.24 | 21.86 | |

TABLE 7

Three stage counter-current extraction of oat pearlings with aqueous ethanol. Five minutes stirring between extraction stages.

| Sample | Wet Weight (g) | Dry Weight (g) | % recovery |
|---|---|---|---|
| Solid 0 | 42.10 | 19.26 | |
| Solid 1 | 45.08 | 18.61 | |
| Solid 2 | 42.25 | 19.34 | |
| Solid 3 | 40.70 | 19.47 | |
| Supernatant 1 | 52.00 | 1.00 | 5.0 |
| Supernatant 2 | 28.72 | 1.29 | 6.5 |
| Supernatant 3 | 43.67 | 1.53 | 7.7 |

TABLE 8

Three stage counter-current extraction of oat pearlings with aqueous ethanol. Twenty-five minutes stirring between separation stages.

| Sample | Wet Weight (g) | Dry Weight (g) | |
|---|---|---|---|
| Solid 0 | 41.88 | 18.63 | |
| Solid 1 | 42.11 | 18.13 | |
| Solid 2 | 41.41 | 18.62 | |
| Solid 3 | 40.82 | 19.3 | |
| Supernatant 1 | 54.58 | 1.10 | 5.5 |
| Supernatant 2 | 31.35 | 1.63 | 8.2 |
| Supernatant 3 | 46.66 | 1.95 | 9.8 |

TABLE 9

Three stage counter-current extraction of hexane extracted oat pearlings with aqueous ethanol. Twenty five minutes stirring between extraction stages.

| Sample | Wet Weight (g) | Dry Weight (g) | % recovery |
|---|---|---|---|
| Solid 0 | 42.23 | 17.82 | |
| Solid 1 | 44.17 | 17.46 | |
| Solid 2 | 43.52 | 17.80 | |
| Solid 3 | 41.87 | 19.22 | |
| Supernatant 1 | 50.61 | 0.90 | 4.5 |
| Supernatant 2 | 28.7 | 1.27 | 6.4 |
| Supernatant 3 | 42.07 | 1.59 | 8.0 |

We claim:

1. A process for producing oat pearlings, oat flour and oat bran products from oat groats, comprising: surface abrading said oat groats so as to remove up to about 15% by weight of said oat groat as surface material, separating said surface material as said oat pearlings from said abraded oat groats, steeping said separated oat groats in an aqueous medium for up to about 4 hours at a temperature up to about 50° C., separating said steeped groats from said aqueous medium, and wet milling said steeped groats in an aqueous alcoholic medium, containing up to about 80% of an aliphatic alcohol, so as to produce a slurry, separating said aqueous alcoholic slurry into an insoluble oat bran product and a soluble endospermic product, and recovering said oat flour from said soluble endospermic product.

2. A process as claimed in claim 1 wherein said aqueous alcoholic medium contains between 40% and 50% ethanol.

3. A process as claimed in claim 1 including the step of extracting said oat pearlings with an organic solvent so as to produce lipase and oat oil.

4. A process as claimed in claim 3 wherein said organic solvent is selected from the group consisting of isopropanol, heptane, acetone, ethyl acetate and hexane.

5. A process as claimed in claim 4 wherein the solvent is hexane.

6. A process as claimed in claim 1 including the step of extracting said oat pearlings with a volatile aqueous polar solvent mixture, separating extracted said oat pearlings from said solvent mixture, removing polar solvent from said solvent mixture so as to produce a liquid or powder fraction which exhibits anti-irritant activity in dermatological tests, and recovering said extracted oat pearlings which are rich in oat oil.

7. A process as claimed in claim 6 wherein said polar solvent is selected from the group consisting of methanol, ethanol and propanol.

8. A process as claimed in claim 7 wherein said polar solvent is ethanol.

9. A process as claimed in claim 1 including the step of extracting said pearlings with a solvent mixture so as to produce an anti-irritant fraction.

10. A process as claimed in claim 9 wherein said solvent mixture comprises glycerol, propylene or butylene glycol.

11. A process as claimed in claim 1 including the steps of extracting said insoluble oat bran product in an aqueous slurry at a temperature in the range 60–100° C., in the presence of alpha amylase, separating the slurry into an insoluble oat bran product and a beta-glucan-containing liquor, and precipitating beta-glucan from said liquor.

12. A process for producing an anti-irritant product and a light oat oil product from oat pearlings comprising: sequentially extracting said pearlings with a volatile aqueous polar solvent; separating extracted pearlings from a solvent mixture containing said anti-irritant, removing said polar solvent from said solvent mixture so as to produce a liquid or powder fraction which exhibits anti irritant activity in dermatological tests, drying the extracted pearlings and re-extracting dried said extracted pearlings with a nonpolar solvent to produce a light oat oil.

13. A process for producing an enriched oat bran and a refined oat flour from pearled oat groats comprising: steeping said pearled oat groats in an aqueous medium for up to about 4 hours at a temperature up to about 50° C., separating the steeped groats from said aqueous medium, and wet milling the steeped groats in an aqueous alcoholic medium, containing up to about 80% of an aliphatic alcohol, so as to produce a slurry, separating said aqueous alcoholic slurry into an insoluble oat bran product and a soluble endospermic product, and recovering said refined oat flour from said soluble endospermic product.

14. A process as claimed in claim 13 including separating said refined oat flour into oat starch and oat protein.

* * * * *